US006574340B1

(12) United States Patent
Bindner et al.

(10) Patent No.: US 6,574,340 B1
(45) Date of Patent: Jun. 3, 2003

(54) METHOD FOR DETERMINING A PARAMETER SET OF A HEARING AID

(75) Inventors: Joerg Bindner, Weisendorf (DE); Eduard Kaiser, Forchheim (DE); Ullrich Sigwanz, Hausen (DE); Roland Weidner, Zapfendorf (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 0 days.

(21) Appl. No.: 09/169,991

(22) Filed: Oct. 13, 1998

(65) Prior Publication Data

(65)

(30) Foreign Application Priority Data

Oct. 14, 1997 (DE) .......................................... 197 45 398

(51) Int. Cl.[7] ........................ H04R 29/00; H04R 25/00; A61B 5/12

(52) U.S. Cl. ........................ 381/60; 381/312; 381/314; 73/585

(58) Field of Search .......................... 381/60, 312, 314, 381/315, 329; 73/585; 600/528, 586

(56) References Cited

U.S. PATENT DOCUMENTS 5,386,475 A * 1/1995 Birch et al. .................... 381/68
5,825,611 A * 10/1998 Kaiser et al. ............... 381/321

FOREIGN PATENT DOCUMENTS

EP 0 064 042 1/1986

* cited by examiner

*Primary Examiner*—Forester W. Isen
*Assistant Examiner*—Elizabeth McChesney
(74) *Attorney, Agent, or Firm*—Schiff Hardin & Waite

(57) ABSTRACT

In a method for determining a parameter set for a hearing aid during the computerized setting of the hearing aid, a macro call is determined, the macro call is converted into at least one setting command according to a macro definition, and the parameter set is determined dependent on the at least one setting command. Such a method is high-performance and nonetheless flexible and easy to manipulate.

16 Claims, 3 Drawing Sheets

METHOD FOR DETERMINING A PARAMETER SET OF A HEARING AID

BACKGROUND OF THE INVENTION

1. Field of the Invention

The present invention is directed to a method for determining a parameter set of a hearing aid.

2. Description of the Prior Art

In a modern hearing aid as disclosed, for example, in European Application 0 064 042, the amplification and transmission properties can be set with a number of parameters. A number of parameter sets that are referred to as auditory or hearing programs are stored in the hearing aid. During fitting of the hearing aid, these auditory programs are determined by a hearing aid acoustician using a computer. When wearing the hearing aid, the user selects one of the auditory programs dependent on the current auditory situation.

With increasing performance capability of the hearing aids, however, the number of parameters to be set also increases. Up to 32 or even more parameters and up to 8 programs are provided given high-performance devices with digital signal processing. The parameters, which are also referred to as "actuators", relate to properties such as the amplification of the hearing aid in a number of frequency ranges, corner frequencies for limiting these frequency ranges and amplification dependent on input level (AGC—automatic gain control) in a number of frequency ranges, controllers for setting the unwanted noise suppression and the channel coupling, etc.

These parameters are oriented to the technical structure of the hearing aid, so that the audiological effect of a modification of one of the parameters is often not easy to survey. Further, some parameters mutually influence one another, for example the actuators for the gain of the hearing aid in specific frequency ranges and what are referred to as the NH/NL actuators that relate to the gain for low or high frequencies. Further, there are dependencies between the individual auditory programs such that modifications of a parameters in one auditory program influence the other auditory programs.

Due to these difficulties and due to the high number of parameters to be set, which, moreover, are different for every hearing aid type, the optimum fitting of a hearing aid is a very complex and time-consuming task that requires extensive knowledge and experience with the specific hearing aid type on the part of the hearing aid acoustician. In turns out in practice that many hearing aids are not optimally set. Similar difficulties occur when a predetermined parameter set is to be modified in order to eliminate a deficiency that still exists. Dependent on the hearing aid type, very different approaches are also meaningful, so that special knowledge is likewise required.

For fitting a hearing aid, it is known to employ a hearing aid setting program that contains fixed adaptation and correction algorithms. Such programs, however, are very inflexible and are only updated at relatively long time intervals. Recent experience therefore only enters into the program given a software update. Experienced hearing aid acousticians also criticize such programs because the algorithms cannot be modified for the user and the user therefore cannot apply his or her own know how.

SUMMARY OF THE INVENTION

An object of the present invention, accordingly, is to avoid the aforementioned problems and offer a method for determining a parameter set of a hearing aid that is high-performance and nonetheless flexible and simple to manipulate.

The above object is achieved in accordance with the principles of the present invention in a method for determining a parameter set for the computerized setting of a hearing aid, including the steps of determining a macro call in the computer, converting the macro call into at least one setting command for the hearing aid according to a macro definition, and determining the parameter set dependent on the aforementioned setting command.

The invention proceeds from the basic idea of making macro calls available to the user. As a result of these macro calls, a number of setting commands for parameters of the hearing aid can be combined to command sequences that implement a function that the user can understand. The hearing aid-oriented significance of the individual parameters and setting commands can thus be converted into a user-oriented or task-oriented significance with a suitable set of macro definitions. Each macro call can thereby implement a relatively complex setting function. This facilitates the setting of the hearing aid by the hearing aid acoustician as well as by a technically knowledgeable user.

Macro definitions are usually not an integral component part of a program but are separate from the program logic and the actual program execution. Therefore they can be quickly modified given employment in a hearing aid setting program without a new version of the hearing aid setting program having to be produced. When a suitable tool is available, existing macro definitions can be modified with relatively little outlay and little familiarization time. For example, a hearing aid acoustician or a distribution organization of the hearing aid manufacturer can adapt predetermined macro definitions to their own requirements. The individual know how can thereby be taken into consideration. Suitable macro sets can also be quickly designed for new hearing aid types.

In some embodiments of the invention, there can be a certain dependency between the hearing aid setting program and the macro definitions, for example a number of components can be united to form a common datafile. Preferably, however, the macro definitions can be modified independently of the hearing aid setting program, and, in further preferred embodiments, they are even stored in a datafile or data table that is separate from the hearing aid setting program. An especially good separation between the actual hearing aid setting program, which cannot be modified by the user, and the macro definitions adaptable by the user (possibly with an auxiliary program) is thus achieved.

Comfortable possibilities for ordering and classifying the individual macros and for calling by the user are preferably provided. In preferred embodiments, a macro call ensues dependent on a problem description of the user and/or by the user actuating a control panel. The problem description by the user can be comprised in the selection of a question the user is asked and/or in an answer the user gives. In preferred embodiments, these functions related to the user interface and the user prompting are also at least partly modifiable independently of the hearing aid setting program. An especially high flexibility and adaptability to the individual ideas of the user is thus achieved. Information about these functions is preferably stored in at least one datafile or data table separate from the hearing aid setting program.

In preferred embodiments, a macro call—when a corresponding macro definition is present—is converted into a number of setting commands, so that complex functions can be executed with a single macro call. In one preferred development of the invention, a number of setting command groups can be provided in a macro definition, one thereof being selected given the corresponding macro call. This selection preferably ensues dependent on the implementability of the setting commands and/or on a weighting of the setting commands, whereby the implementability of the setting commands is in turn determined by the momentary parameter values. A higher or lower prospect of success is thus allocated to the individual setting command groups—each of which respectively corresponds to a problem solving strategy—and the instruction sequence having the highest prospect of success is selected. A quasi-intelligent behavior of the system that takes the current hearing aid setting into consideration is thus achieved.

In preferred embodiments, the method serves for the modification of a previous parameter set in order to adapt this more exactly to the hearing impairment of the user. The method can be repeatedly implemented, whereby the respectively current parameter set is modified in small steps (incrementally).

DESCRIPTION OF THE PREFERRED EMBODIMENTS

Figure 1:
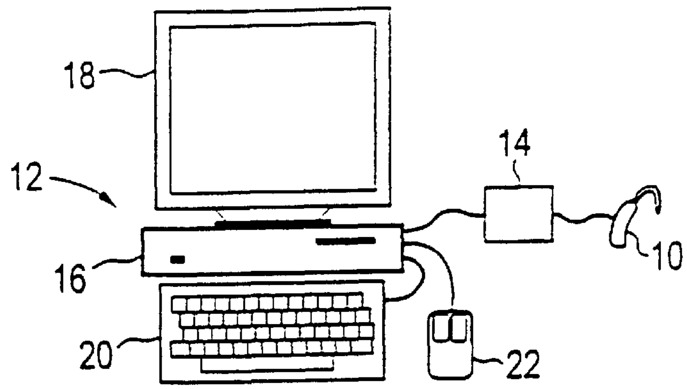
FIG. 1 is an illustration of a system for setting a hearing aid in accordance with the invention.

A known personal computer (PC) 12 is connected to the hearing aid 10 (shown enlarged) via a programming device 14 given the system for programming a hearing aid 10 shown in FIG. 1. The programming device 14 is connected to the computer 12 and to the hearing aid 10 by multi-lead lines. The computer 12 includes a main processor unit 16, a picture screen 18 and input devices such as a keyboard 20 and a mouse 22. The computer 12 runs under a suitable graphics oriented operating system and executes a hearing aid setting program. A user can produce or modify a parameter set for the hearing aid 10 with this setting program. In a known way, parameter sets can be transmitted between the computer 12 and the hearing aid 10 in both directions via the multi-lead lines and the programming device 14.

The hearing aid setting program in accordance with the invention offers macro calls for producing and modifying a parameter set. Each macro call is converted into one or more setting commands dependent on the allocated macro definition. The setting commands in turn define the parameter set in that they either modify a predetermined parameter set or generate a new parameter set.

Figure 2:
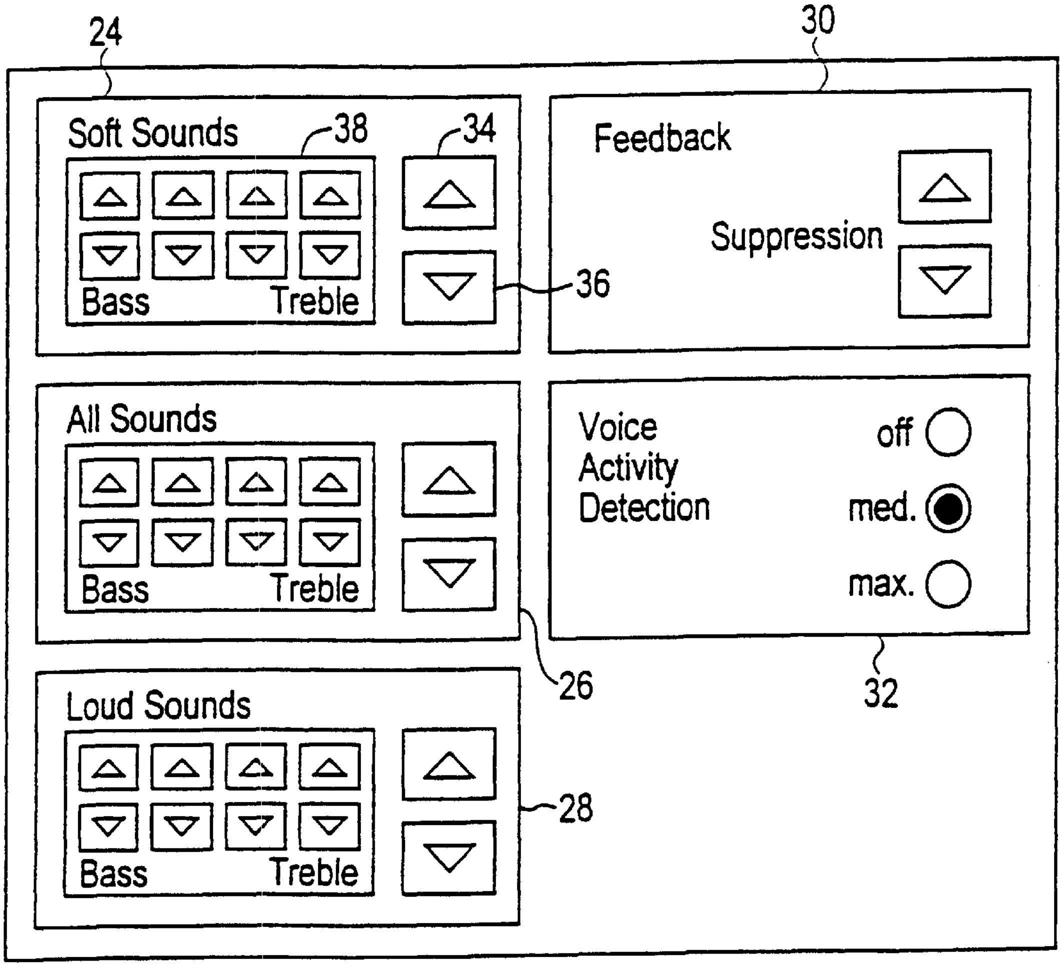
FIG. 2 is an illustration of an exemplary embodiment of a picture screen display with control panels in accordance with the invention.

The user can call a macro in various ways in the operation of the hearing aid setting program. The user can either actuate a control panel shown on the picture screen 18 with the mouse 22 or he or she can call a macro that has been suggested as reaction to a problem description. The first of these possibilities is shown in FIG. 2. This shows a portion of a window shown on the picture screen 18 in which a number of control panel groups 24, 26, 28, 30, 32 are arranged. The control panel group 24 relates to the amplification of quiet input signals. A first control panel 34 is provided for boosting the gain in the entire frequency range. When the user actuates this control panel 34 with a mouse click, a corresponding macro that includes a number of setting commands for setting a plurality of parameters is called. Correspondingly, a second control panel 36 serves for reducing the gain of quiet signals in the entire frequency range. Eight further control panels for increasing and reducing the gain in individual frequency segments are arranged in a region 38. Analogously, the control panel groups 26 and 28 serve for calling macros that set the amplification properties for all input signals or, respectively, loud input signals.

Macros to increase and the reduce the feedback suppression are called with the two control panels of the control panel group 30. The control panel group 32 includes three control panels designed as radio knobs in order to suppress a voice recognition function of the hearing aid by calling a suitable macro or setting it to a medium or maximum value. It can be seen from these examples that each control panel has a single significance oriented to the desired effect. Technical details of the setting commands to be carried out are thus hidden from the user by the macro calls.

Figure 3:
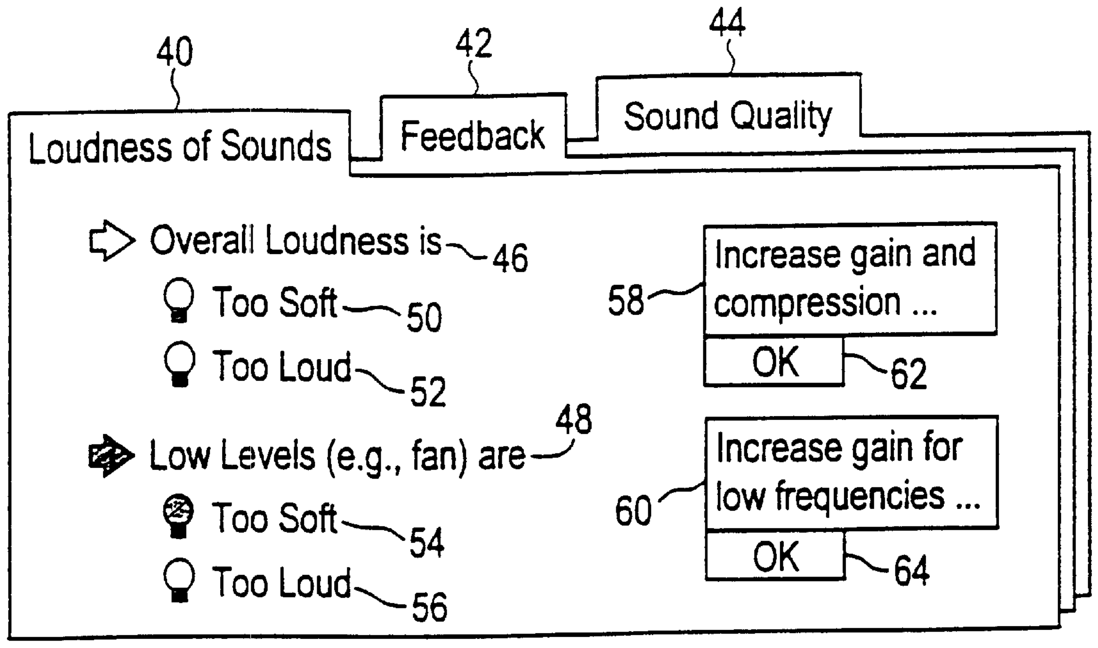
FIG. 3 is an illustration an exemplary embodiment of a picture screen display with questions, proposed answers and macro calls in accordance with the invention.

FIG. 3 illustrates the second of the aforementioned possibilities of a macro call by the user. The hearing aid setting program thereby graphically displays a number of cardfile cards 40, 42, 44 on the picture 18, each of these relating to a respective problem group. For example, the cardfile card 40 serves for solving problems related to the volume of noises, the cardfile card 42 relates to problems of feedback and the cardfile card 44 relates to problems of sound quality.

A tree-like structure of questions and answers with which the user can provide an adequately exact problem description is illustrated on each cardfile card. Thus, a question 46 about the overall volume and a question 48 about the volume of quiet noises is provided on the cardfile card 40. As answers 50, 52, 54, 56, the hearing aid setting program offers the possibilities “too soft” and “too loud” in both instances. More differentiated answers are possible to other questions, for example the answers “always”, “in quiet surroundings”, “while chewing/talking” or “when telephoning” to the question about the occurrence of a feedback.

In the example shown in FIG. 3, the user has selected the question 48 and the answer 54 with respective mouse clicks and has thus described the problem that quiet sounds are transmitted too quietly. In this case, the hearing aid setting program proposes two solutions, each of which corresponds to a macro call. The solutions are displayed into two proposal windows 58, 60. When the user then actuates one of the actuation keys 62, 64, the appertaining macro whose indicator agrees with the proposed solution is executed.

The user interface shown as an example in FIG. 2 and FIG. 3 as well as the individual macro definitions are not predetermined by the hearing aid setting program. On the contrary, this program accesses a number of datafiles of data tables in which all required information with respect to the user interface and the macros are stored.

Figure 4:
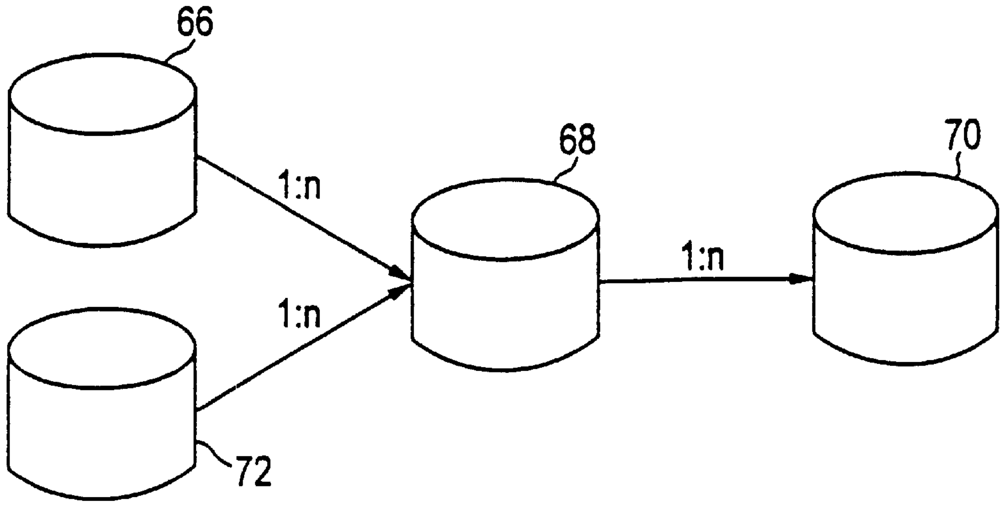
FIG. 4 is an illustration of the data relationships in the inventive method.

The structure of these datafiles is schematically shown in FIG. 4. A question datafile 66 contains the questions to be presented to the user, for example the questions 46, 48 shown in FIG. 3. An answer datafile 68 contains one or more possible answers of the user for each question in the question datafile 66, for example the two answers 54, 56 for the question 48. Finally, a macro datafile 70 with a number of macro definitions is provided, with one macro or a number of macros being allocated to every answer in the answer datafile 68.

Information relating to the control elements shown in FIG. 2 is stored in a control element datafile 72. In general, a number of contextually affiliated control panels form an entry in the control element datafile 72, and the individual control panels each respectively correspond to an answer in the answer datafile 68. Thus, for example, the two control panels 34, 36 are combined to one control element in the control element datafile 72 and are connected to two answers, "boost gain" and "reduce gain", in the answer datafile 68. Likewise, a single entry in the control element datafile 72 and three answers in the answer datafile 68 are allocated to the three radio knobs of the control panel group 32. Further types of control elements, for example check-off fields, selection lists, etc., can be provided in the control element datafile 72. Further, information about the grouping and arrangement of the control elements on the picture screen 18 is contained therein.

The datafiles 66, 68, 70, 72 are not a component of the actual hearing aid setting program. In particular, they can be produced or modified separately from this program without having to newly compile the hearing aid setting program. An auxiliary program for the comfortable editing of the datafiles 66, 68, 70, 72 is provided for this purpose. New perceptions can quickly flow into the user interface, the user prompting and the macro definitions with the auxiliary program without having to generate a new version of the hearing aid setting program. The datafiles 66, 68, 70, 72 can be produced and/or modified both by the manufacturer of the overall system as well as by third-party vendors or by hearing aid acousticians.

Figure 5:
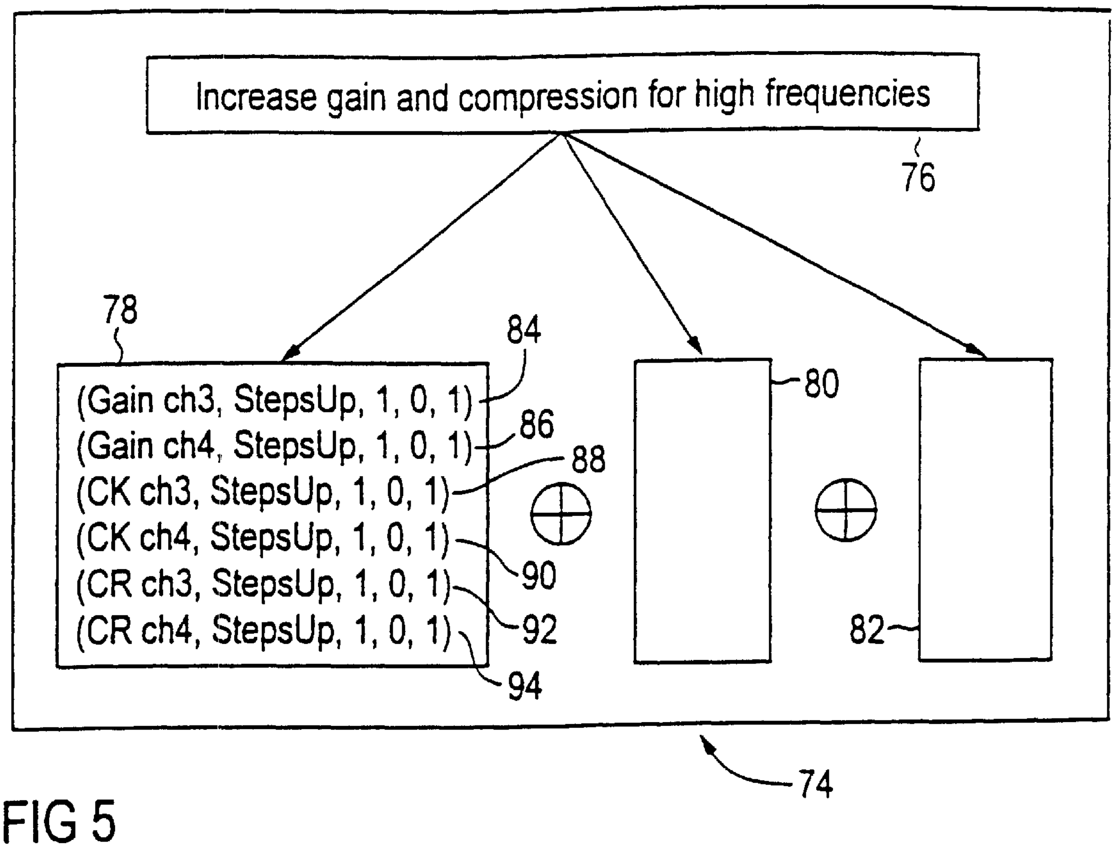
FIG. 5 is an illustration of an exemplary macro definition.

As an example, FIG. 5 shows a macro definition 74 contained in the macro datafile 70. An indicator 76 describes the function of the macro, i.e. the boosting of the gain and compression for high frequencies here. Further, the macro definition 74 comprises three alternative setting command groups 78, 80, 82. The first setting command group 78 contains six setting commands 84, 86, 88, 90, 92, 94, whereas the content of the other two setting command groups 80, 82 is not shown in greater detail in FIG. 5. In the exemplary embodiment described here, each macro definition comprises one, two or three setting command groups 78, 80, 82, and each setting command group 78, 80, 82 can contain up to 64 setting commands 84, 86, 88, 90.

In general, a setting command 84, 86, 88, 90, 92, 94 can be written as follows as a quintuple:

(COMMAND, SUB-COMMAND, VALUE1, VALUE2, WEIGHTING)

The component COMMAND thereby indicates the type of setting command. A separate setting command is thus provided for each of the, for example, 32 parameters of the hearing aid 10 in order to designationally set or modify this parameter. The component SUB-COMMAND specifies the setting command more precisely, for example by indicating the direction of a modification of a parameter and a measure of the modification (in steps, in decibels, to a maximum or minimum value, to an absolute value, etc.). The components VALUE1 and VALUE2 contain arguments for the setting command, for example the number of steps or the new parameter value to be set. Finally, the component WEIGHTING is provided that recites a measure for the importance of this setting command and is employed in order, given a macro call, to select one of a number of alternative setting command groups 78, 80, 82 as warranted. For example, the setting command 84 in FIG. 5 effects a boost of the gain parameters for the frequency channel 3 ("Gain ch3") by one step.

Setting commands that simultaneously modify a number of parameters exist in addition to the previously described setting command for one respective parameter of the hearing aid 10. For example, all parameters are set according to a predetermined, heuristic algorithm corresponding to an audiogram of the patient by the control command (BestFit, 0, 0, 0, w). Further, a command ChannelAdjust is provided that influences the gain and compression parameters of the hearing aid 10. This control command deviates from the form previously described because it includes twelve parameters that specify what modifications should be undertaken on what channels and for which input levels.

Finally, setting commands are provided for the conditional execution of parts of a macro. For example, the overall gain is boosted by 12 dB by the following setting commands if it was originally higher than 5 dB but is boosted by only 3 dB otherwise:

(if, Gain, GT, 5, w1)
  (Gain, dBUp, 12, 0, w2)
(else, 0, 0, 0, w3)
  (Gain, dBUp, 3, 0, w4)
(endif, 0, 0, 0, 0).

In the execution of the hearing aid setting program, the user triggers a macro call by actuating a control panel 34, 36 in FIG. 2 or an actuation key 62, 64 in FIG. 3. The allocated macro definition 74 is read from the macro datafile 70. If the macro definition contains only one setting command group, the setting commands contained therein are executed in sequence in order to modify or overwrite the previous parameter set. If, however, the macro definition 74, as shown in FIG. 5, contains a plurality of alternative setting command groups 78, 80, 82, then one thereof is automatically selected by the hearing aid setting program.

For this selection, all setting commands in the setting command groups 78, 80, 82 are investigated in view of their implementability. A setting command is considered not implementable or only partly implementable when it requires a modification of a parameters that would exceed a predetermined range of adjustment of this parameter. Further, setting commands that would result in inadmissible side-effects on other auditory programs are not executed. The weightings (component WEIGHTING) of the implementable setting commands (and percentage weightings for the only partly implementable setting commands) are then summed for each setting command group 78, 80, 82. Given setting commands that set a parameter to a fixed value, the weighting can also depend on the extent of the modification compared to the previous parameter value.

The setting command group 78, 80, 82 having the highest weighting sum of implementable setting commands is executed. Macros can thus be defined whose effect is dependent on the momentary configuration of the hearing aid 10.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining a parameter set for computerized setting of a hearing aid, comprising the steps of:

(a) determining and storing a macro call in a computer, said macro call consisting of a save sequence of commands recalled with a single entry into said computer;

(b) converting the commands in said macro call in said computer into at least one setting command for a hearing aid according to a macro definition; and (c) determining a parameter set in said computer for said hearing aid dependent on said at least one setting command.

2. A method as claimed in claim 1 comprising the additional step of setting said hearing aid using a setting program, and incorporating steps (a), (b) and (c) into said hearing aid setting program.

3. A method as claimed in claim 2 comprising the additional step of storing said macro definition in a data file of a data file table separate from said hearing aid setting program for allowing modification of said macro definition independently of said hearing aid setting program.

4. A method as claimed in claim 2 comprising the additional step of providing a user-actuatable control panel for operating said computer, and wherein step (a) comprises determining said macro call by actuation of said control panel.

5. A method as claimed in claim 4 wherein said control panel has modifiable properties associated therewith, and comprising the additional steps of storing at least some of said modifiable properties of said control panel in a data file of a data file table separate from said hearing aid setting program, and modifying at least some of said modifiable properties of said control panel dependent on said hearing aid setting program.

6. A method as claimed in claim 4 comprising the additional step of conducting a question and answer dialogue with a user via said control panel to obtain a dialogue result, and wherein step (a) comprises determining said macro call dependent on said dialogue result.

7. A method as claimed in claim 6 comprising the additional step of modifying at least a portion of said question and answer user dialogue independently of said hearing aid setting program, and storing questions and answers of said question and answer user dialogue in at least one data file of a data file table separate from said hearing aid setting program.

8. A method as claimed in claim 1 wherein step (b) comprises converting said macro call into a plurality of setting commands.

9. A method as claimed in claim 8 wherein step (b) comprises converting said macro call into a plurality of alternative setting commands.

10. A method as claimed in claim 9 wherein said alternative setting commands are individually implementable by respectively different degrees, and comprising the additional step of selecting one of said alternative setting commands dependent on the degree to which said one of said alternative setting commands is implementable.

11. A method as claimed in claim 9 wherein each of said alternative setting commands has a different weighting respectively associated therewith, and comprising the additional step of selecting one of said alternative setting commands dependent on the weighting associated therewith.

12. A method as claimed in claim 8 wherein step (b) comprises converting said macro call into a plurality of alternative groups of setting commands.

13. A method as claimed in claim 12 wherein said alternative groups of setting commands are individually implementable by respectively different degrees, and comprising the additional step of selecting one of said alternative groups of setting commands dependent on the degree to which said one of said alternative groups of setting commands is implementable.

14. A method as claimed in claim 12 wherein each of said alternative groups of setting commands has a different weighting respectively associated therewith, and comprising the additional step of selecting one of said alternative groups of setting commands dependent on the weighting associated therewith.

15. A method as claimed in claim 1 wherein step (c) comprises determining said parameter set by modifying a previous parameter set according to said at least one setting command.

16. A method as claimed in claim 11 comprising the additional steps of successively conducting steps (a), (b) and (c) multiple times with each repetition producing a parameter set which is modified in a successive repetition dependent on said at least one setting command in the successive repetition.

* * * * *